(12) United States Patent
Kurzweil et al.

(10) Patent No.: US 8,560,044 B2
(45) Date of Patent: Oct. 15, 2013

(54) GARMENT ACCESSORY WITH ELECTROCARDIOGRAM SENSORS

(75) Inventors: Raymond C. Kurzweil, Newton, MA (US); Paul Albrecht, Bedford, MA (US); Lucy Gibson, Wellesley Hills, MA (US); Amara Angelica, Webster, NY (US); Aaron Kleiner, West Newton, MA (US)

(73) Assignee: Medicomp, Inc., Melbourne, FL (US)

( * ) Notice: Subject to any disclaimer, the term of this patent is extended or adjusted under 35 U.S.C. 154(b) by 982 days.

(21) Appl. No.: 11/749,248

(22) Filed: May 16, 2007

(65) Prior Publication Data

US 2008/0287769 A1 Nov. 20, 2008

(51) Int. Cl.
*A61B 5/0408* (2006.01)
*A61B 5/0416* (2006.01)

(52) U.S. Cl.
USPC .......................... 600/386; 600/382; 600/509

(58) Field of Classification Search
USPC .......... 600/382–393, 509; 450/11, 26, 30–35, 450/89
See application file for complete search history.

(56) References Cited

U.S. PATENT DOCUMENTS

| | | | |
|---|---|---|---|
| 4,243,052 A | 1/1981 | Bailey | |
| 4,381,012 A * | 4/1983 | Russek | ......................... 600/382 |
| 5,353,793 A | 10/1994 | Bornn | |
| 5,445,149 A | 8/1995 | Rotolo et al. | |
| 6,047,203 A | 4/2000 | Sackner et al. | |
| 6,102,856 A | 8/2000 | Groff et al. | |
| 6,205,346 B1 | 3/2001 | Akiva | |
| 6,341,504 B1 | 1/2002 | Istook | |
| 6,477,397 B1 | 11/2002 | Ronkainen et al. | |
| 6,551,252 B2 | 4/2003 | Sackner et al. | |
| 6,668,380 B2 | 12/2003 | Marmaropoulos et al. | |
| 6,755,795 B2 | 6/2004 | Marmaropoulos et al. | |
| 6,807,438 B1 | 10/2004 | Brun Del Re et al. | |
| 6,912,414 B2 | 6/2005 | Tong | |
| 6,930,608 B2 | 8/2005 | Grajales et al. | |
| 2003/0135127 A1 | 7/2003 | Sackner et al. | |
| 2003/0212319 A1 | 11/2003 | Magill | |
| 2004/0073104 A1 * | 4/2004 | Brun del Re et al. | ......... 600/372 |
| 2005/0043641 A1 * | 2/2005 | Ueda | .............................. 600/509 |
| 2005/0049515 A1 | 3/2005 | Misczynski et al. | |
| 2005/0059896 A1 | 3/2005 | Drakulic | |
| 2005/0119701 A1 | 6/2005 | Lauter et al. | |
| 2005/0228234 A1 | 10/2005 | Yang | |

(Continued)

FOREIGN PATENT DOCUMENTS

| | | |
|---|---|---|
| CA | 2 324 713 | 4/2001 |
| GB | 2 388 196 | 11/2003 |

(Continued)

*Primary Examiner* — Lee S Cohen
*Assistant Examiner* — Erin M Cardinal
(74) *Attorney, Agent, or Firm* — Mark R. Malek; Keith Olinga Mitchell; Zies Widerman & Malek

(57) ABSTRACT

A garment accessory includes a member having first and second ends, with the length of the member between the first and second ends being less than the circumference of a subject that the member is configured for and a pair of fastener mechanisms disposed in proximity to the first and second ends of the member, the fastener mechanisms configured to attach the member to an article of clothing worn by a subject. The garment accessory also includes at least a pair of sensors supported by the member with the sensors being at least one of ECG sensors, motion sensors, body temperature sensors and impedance plethysmography sensors.

30 Claims, 15 Drawing Sheets

(56) References Cited

U.S. PATENT DOCUMENTS

2005/0275416 A1 12/2005 Hervieux et al.
2006/0069320 A1 3/2006 Wolff et al.
2006/0135863 A1 6/2006 Birnbaum et al.
2006/0211934 A1 9/2006 Hassonjee et al.

FOREIGN PATENT DOCUMENTS

| WO | WO 02/30279 | 4/2002 |
| WO | WO 2005/053532 | 6/2005 |
| WO | WO2006111875 A1 | 10/2006 |

* cited by examiner

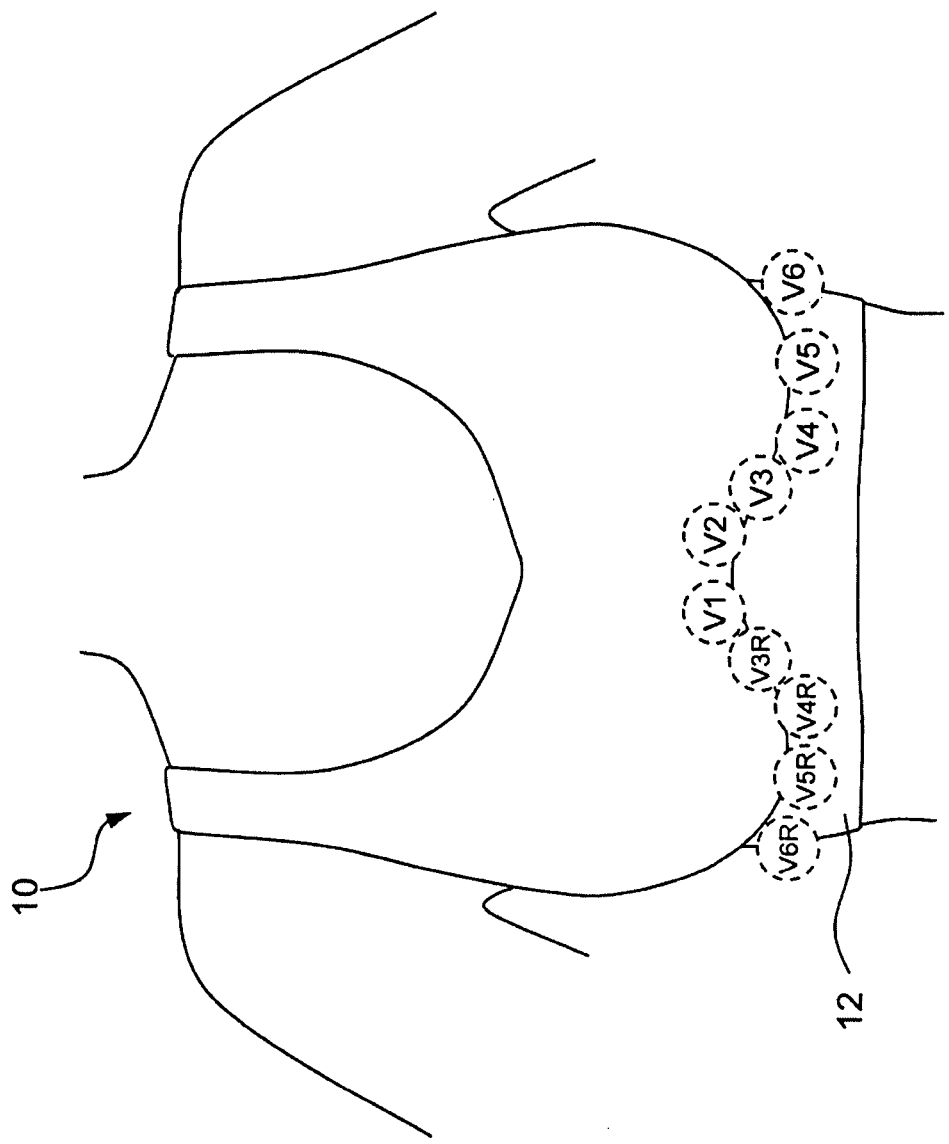

GARMENT ACCESSORY WITH ELECTROCARDIOGRAM SENSORS

BACKGROUND

The present invention relates to electrocardiogram (EGG) monitoring, and in particular to a wearable device with integrated ECG sensors for ambulatory ECG monitoring.

Heart disease is a leading cause of death in the United States. Some patients would benefit from long-term ECG monitoring outside of a clinical setting. For example, atrial fibrillation and myocardial ischemia may occur episodically. Some episodes may occur without patient symptoms. Myocardial ischemia, if persistent and serious, can lead to myocardial infarction (heart attack). During a myocardial infarction, electrophysiological changes are usually seen on the ECG. For accurate diagnosis and effective treatment of many episodic heart conditions, it is useful to know the frequency and duration of such episodes, in a timely manner.

In conventional long-term ECG monitoring, such as with continuous Holter monitors or event monitors, the skin is prepared by a technician. Chest hair may be shaved or clipped from men. The skin is abraded to remove dead skin cells, and cleaned. Abrading often leaves the skin irritated. A technician trained in electrode placement applies the electrodes to the skin with an adhesive. The monitor can be worn for up to a month.

Each electrode of such conventional monitors is attached to an insulated wire that is routed to an amplifier to amplify the ECG signal. The patient has to take care not to pull on the wires connected to the electrode, because the electrode could be pulled off the skin. Removing the electrode with its strong adhesive may be painful. Many electrodes also use a gel next to the skin to improve conductivity of connection of the metal electrode to the skin. Prolonged exposure to the gel can irritate the skin.

SUMMARY

Aspects of the present invention include a garment accessory including a member having first and second ends, with the length of the member between the first and second ends being less than the circumference of a subject that the member is configured for, a pair of fastener mechanisms disposed in proximity to the first and second ends of the member, the fastener mechanisms configured to attach the member to an article worn by a subject and at least a pair of sensors supported by the member.

The following are embodiments within the scope of the invention.

The member further has a fastener mechanism disposed at the center of the member. The fastener mechanisms at the first and second ends of the member and the central portion of the member are configured to couple the member to a brassiere. The pair of sensors are removable from the member. The garment accessory further includes a circuit arrangement electrically coupled to the pair of sensors, the circuit arrangement carried by the member. The fastener mechanism is at least one of hooks, clips, elastic band, hook and loop fasteners and snaps. The fastener mechanism includes a hook mechanism which hooks over a portion of an article of clothing. The fastener mechanism includes a set of clips disposed on the bottom outside edge of the garment accessory, configured such that when the garment accessory is underneath an article of clothing that encircles the torso of a subject, the clips attach to the bottom edge of the article of clothing.

The circuit arrangement includes a wireless transmitter. The sensors are at least one of ECG sensors, motion sensors, body temperature sensors and impedance plethysmography sensors. The garment accessory is configured to attach to a brassiere. At least part of the garment accessory is held in place underneath the lower portion of the front and sides of a brassiere. The part of the assembly is held in place by a pouch or loop portion of a bra. The garment accessory is configured to be secured on side straps of a brassiere. Each of the sensors include a sensor membrane in electrical contact with the mating snap, the sensor membrane comprised of an electrically conductive, flexible material. The sensor membrane is comprised of conductive rubber or conductive silicone. The sensor membrane has a major surface thereof that is exposed to make contact with the skin of a subject, the major surface being curved. The sensor membrane has a major surface thereof that is exposed to make contact with the skin of a subject, the major surface being flat. The sensor membrane has the major surface covered with a conductive gel film. The garment accessory further includes a snap comprised of an electrically conductive material disposed in intimate contact with the backside of the sensing membrane to provide an electrical path for a signal from the sensing membrane, the snap engaging a mating snap supported by the strap member. The sensor further includes a sensor frame comprised of a firm, flexible material supporting the sensor membrane. The sensor membrane includes a water resistant material to induce sweat. The garment accessory further includes a layer of sweat-absorbing material disposed adjacent to the sensor membrane.

Additional aspects of the present invention include a brassiere including at least one accommodation disposed on a portion of the brassiere for holding at least a pair of sensors and a pair of detachable sensors carried by the at least one accommodation.

Additional aspects of the present invention include a brassiere-based heart monitor device including a fastener mechanism that attaches the brassiere-based heart monitor device to a brassiere worn by a subject, the brassiere-based heart monitor device including a pair of physiological sensors and an electrical circuit arrangement electrically coupled to the pair of sensors.

One or more aspects of the present invention may provide one or more of the following advantages.

Some embodiments of the device attach to a variety of off-the-shelf bra styles and models. Whereas, other embodiments of the device attach to bras having accommodations for the device, such as pouches to hold part or all of the device, loops to hold part of the device, or slits for part of device to pass through and be held in place with the assistance of the bra. Bras can be worn with or without the device attached.

The heart monitor device is unobtrusive under clothes and comfortable enough to be worn all day for continuous ECG monitoring. The device includes at least two ECG sensors made of comfortable materials and held in place between the bra and the user's skin. Generally the sensors are located in the area of the bra's chest band. The sensors are wired to an electronics module that includes one or more ECG amplifiers and a transmitter for wireless transmission of the ECG, heart rate, or other derived data to a nearby computing device. The heart monitor device includes a battery to power the electronics. In most embodiments the housing material is flexible to be comfortable against the body and thin to provide a low profile under or next to the bra. The device could be a flexible assembly or could have sensors attached by wires to an electronics module.

The device and bra cooperate as a system to provide ECG, with the bra providing tension to hold sensors reliably close to the skin, while providing access to those locations on the body known for high-quality ECG signal characteristics. Tension from the bra helps to keep the sensors from sliding across the surface of the skin. The device may be held in place solely by the tension of the bra or the device may include mechanisms for attachment to the bra, including, for example, a high friction material against the bra and/or the skin, hooks to hang onto the bra, or clips to attach to the bra.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 15 is view depicting lead configurations.

DETAILED DESCRIPTION

Figure 1:
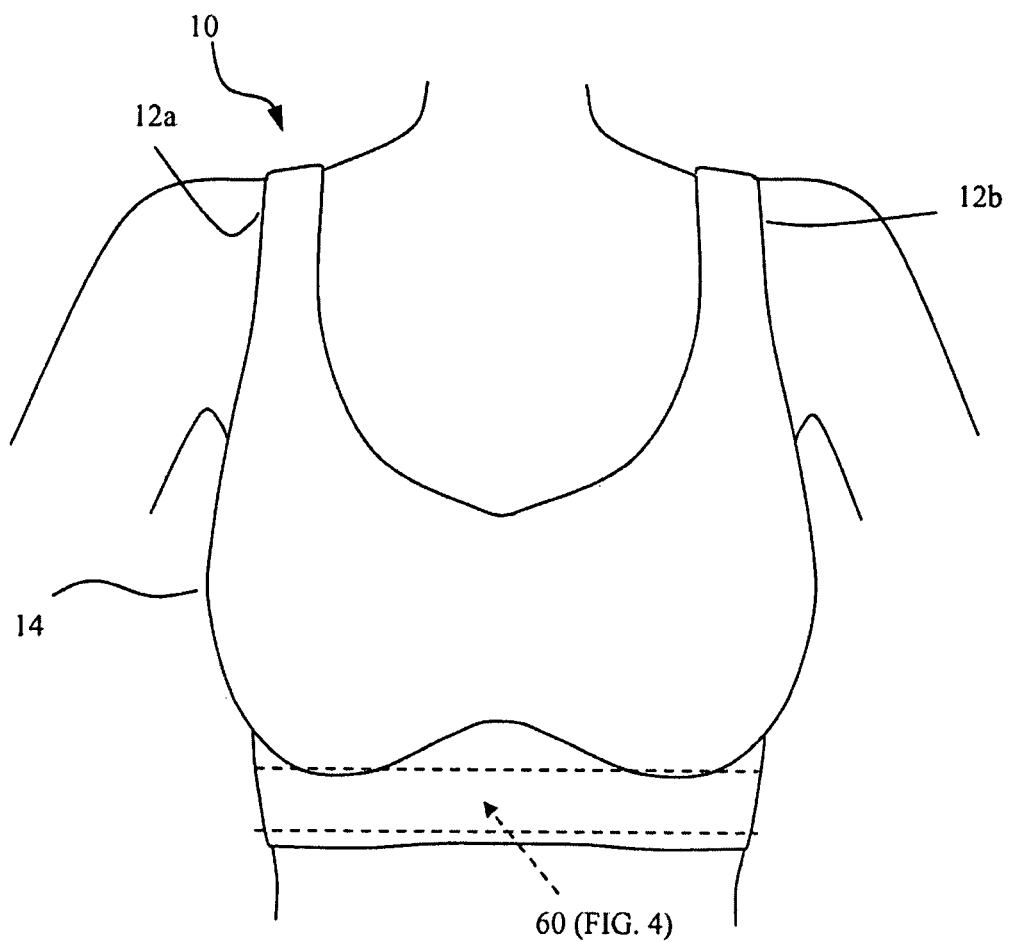
FIG. 1 is a front view of a bra on a female torso with an attachable monitor.
Figure 2:
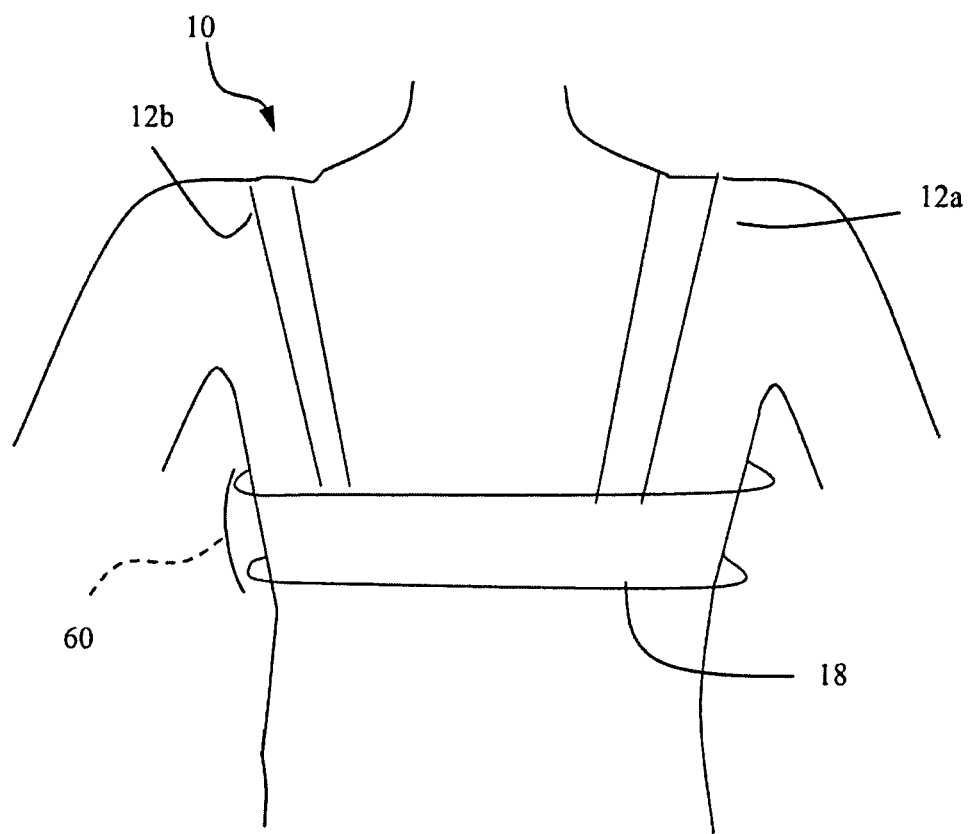
FIG. 2 is the back view of the bra of FIG. 1.

Referring to FIGS. 1 and 2, a bra 10 with a removably attached monitor device 60 carrying physiological sensors is shown. The bra 10 is shown being worn on a female subject, but the bra 10 could be worn by a male with cups appropriately dimensioned.

The bra 10 includes a front portion 14 comprising bra cups from which a pair of shoulder strap portions 12a, 12b emanate that rest over shoulders of the subject and terminate at a back portion 18 of the bra 10. The strap portions 12a, 12b extend over the shoulders and meet at the hack portion 18 that rests against the back of the subject, as shown in FIG. 2.

Figure 3:
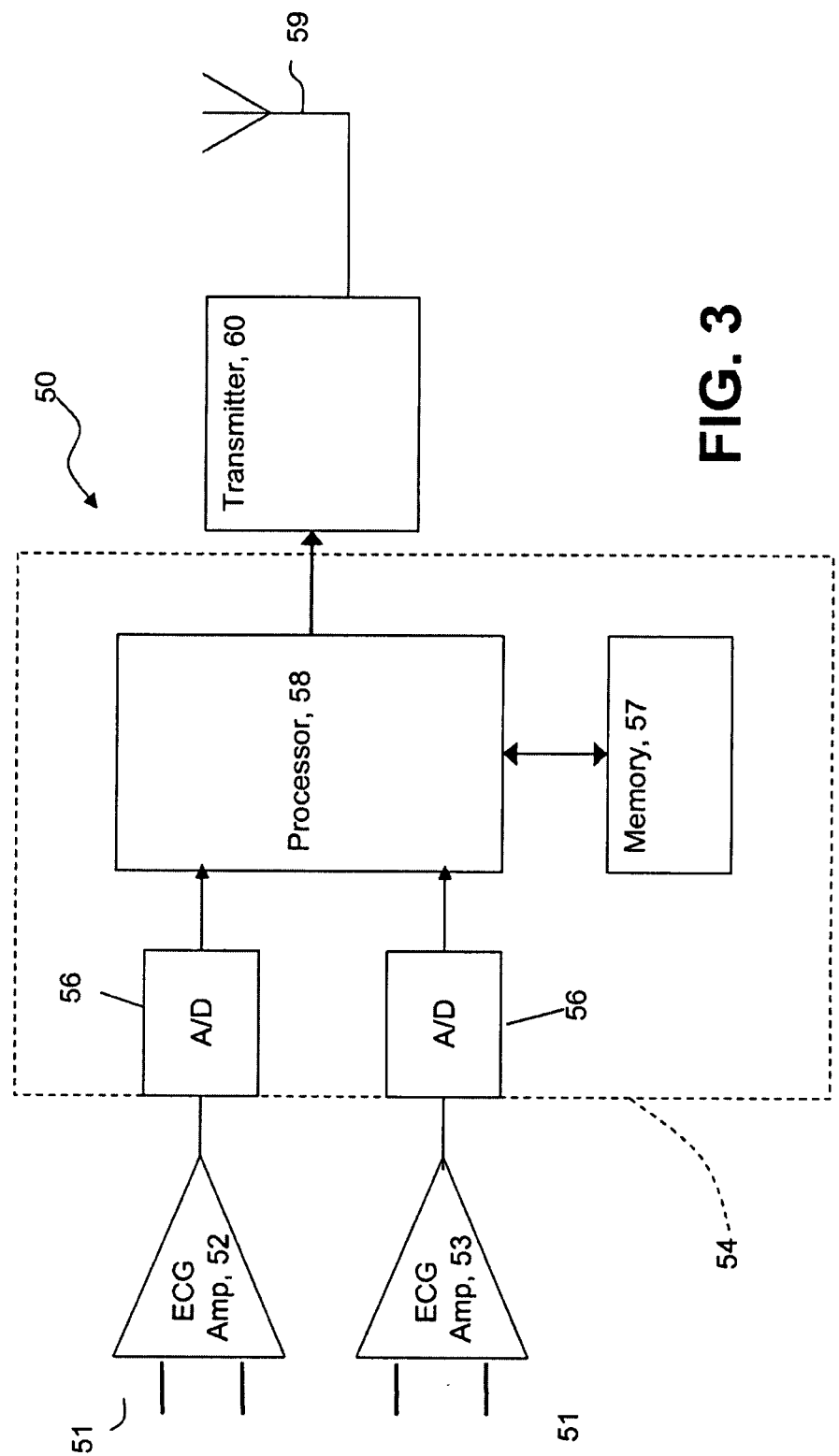
FIG. 3 is a block diagram of a typical circuit arrangement.
Figure 4:
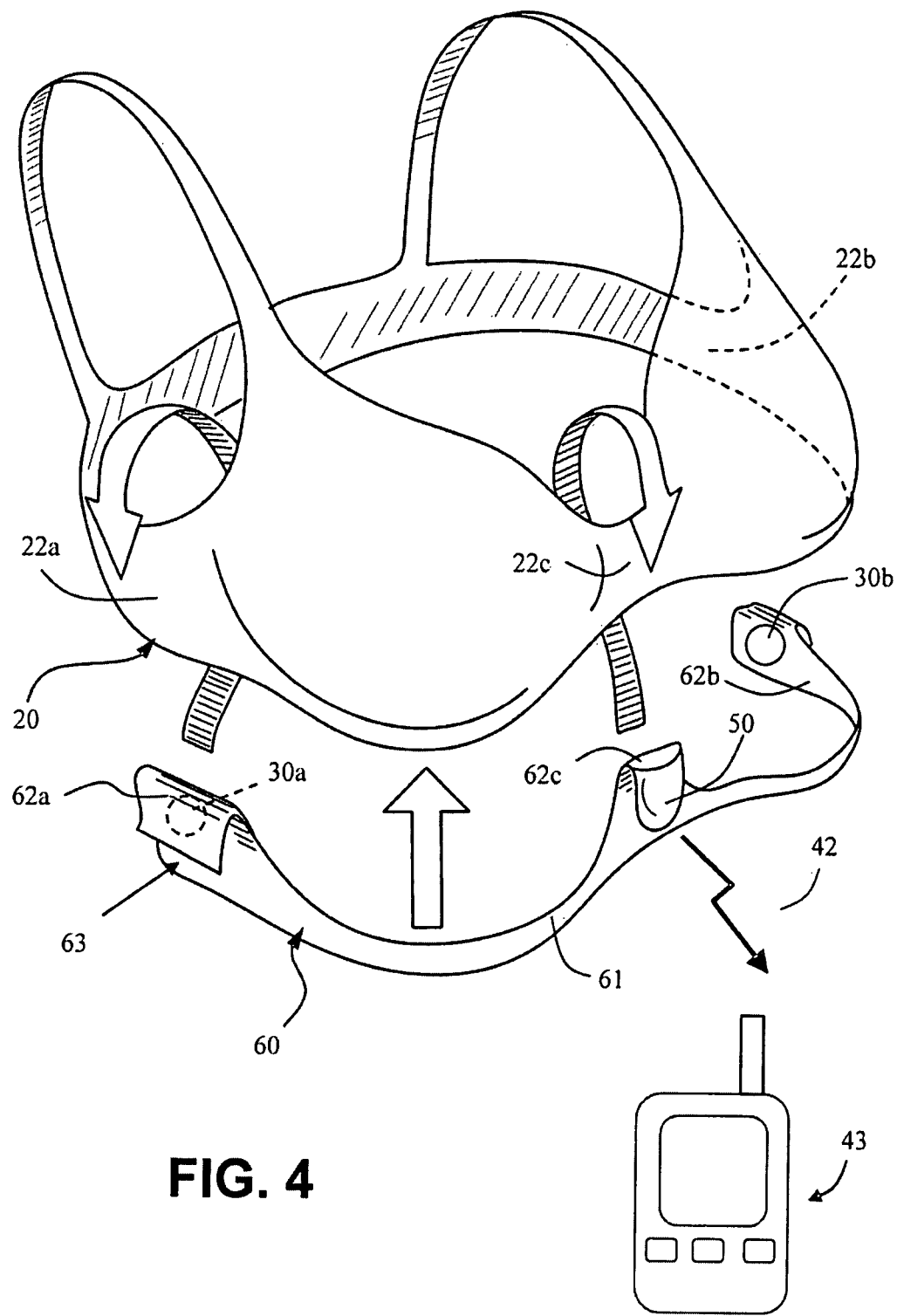
FIG. 4 is a perspective view of the bra with attachable monitor.

The bra 10 supports a plurality of sensors carried by the monitoring device 60 (FIG. 4). The monitor device 60 can also have an electronics module 50 (FIG. 3) that can wirelessly transmit signals from the sensors to a nearby computer, PDA or wireless phone. A PDA 43, as shown in FIG. 4, may be carried by the person wearing the bra 10. Although the sensors described herein will be principally ECG sensors, it is to be understood that the sensors can be any type of physiological type sensor such as motion sensors, body temperature sensors and impedance plethysmography sensors, and so forth.

Referring to FIG. 3, the electronics module 50 typically includes input connectors 51 that are connected to signal amplifiers 52-53. Each amplifier is connected to two sensors to create one ECG lead. Thus in the configuration of FIGS. 3, 4 individual sensors could be connected to the 4 inputs, or 3 sensors could be used, with one sensor connected to the input of 2 different amplifiers. For a system with two sensors, only one ECG amplifier 52 and A/D converter 56 is needed. The amplifiers receive signals from sensors, via an integrated wiring system. The signals from the sensors are amplified, and the amplified signals from these amplifiers are fed into pre-processing circuitry 54 that prepares the signals for transmission and subsequent processing.

The pre-processing circuitry 54 can include A/D converters 56 to digitize the signals from the amplifiers, and may optionally include filters to filter the signals or perform signal processing and identification of physiological conditions. The pre-processing circuitry 54 includes a memory 57 and a processor 58 to implement filtering and processing functions to provide intermediate results and to store information before transmission. Other circuitry is not shown; for instance, timing, storage, interface circuitry and so forth.

The pre-processing circuitry 54 couples the pre-processed signals to a transmitter 60 and antenna 59 that transmits the signal to a base station 43 (FIG. 4). The signal may be transmitted using, for example, Zigbee or Bluetooth protocols, to a base station that can be a computer, PDA (as in FIG. 4) or wireless phone and so forth.

An example of an electronic module is the Alive heart monitor by Alive Technologies Pty. Ltd., (International publication No. WO2005/048830). The Alive heart monitor receives an ECG signal from 2 sensors, amplifies the signal, digitizes the signal, and transmits the signal via the Bluetooth protocol.

Typically, the electronics module 50 is an integral part of the device 60. An alternative is to enclose the electronics module 50 in a case that can be removed from the device 60, and reattached using connectors 51. The electronics module is powered by a battery, which is typically removable from the electronics module 50 for replacement, but alternatively can be permanently sealed in the electronics module 50.

In some configurations, the sensors are coupled to an analog multiplexer and the output of the multiplexer can be coupled to an amplifier. In that configuration a circuit (not shown) selects which sensor to couple through the analog multiplexer.

There are several scenarios for how the monitor device might be used, including, for example, chat signals might be analyzed by the PDA/phone and transmitted to a monitoring center for analysis by a physician.

The monitoring device 60 attaches to any suitable garment that tightly encircles the torso or other parts of the body, for example, certain types of clothing for instance, a bra, or a chest strap, a tight chest harness (e.g. sports or military accessory), and so forth.

Many types of commercial and military chest harness, have characteristics to suitably hold the monitoring device 60 tightly against the skin and hold sensors in useful positions for ECG or other physiological monitoring functions, for example, mountain climbing chest harness, cave exploration chest harness, medical monitoring harness (e.g. breathing monitor), chest harness for camera, military chest harness, radio chest harness, rescue harness.

Referring to FIG. 4, a monitor device 60, i.e., a garment accessory, which is attachable to an article of clothing such as a conventional bra 20, is shown. The monitor device 60 is configured to attach to a variety of off-the-shelf articles of clothing such as a chest strap or a bra. Attached to a bra 20 of the basic type shown in FIG. 4, the bra 20 does not need any modifications to work with the device 60. Other embodiments that work with modified bras 20 are discussed below. In some embodiments, in FIG. 4 (and FIGS. 5 and 6), for example, the garment accessory 60 (FIG. 4) has a length between first and second ends (tabs 62a, 62b) that is approximately half of the circumference of the chest of a subject that the member is configured to be positioned on.

The monitor device 60 is comprised of a thin, firm, flexible band 61 of material that may be similar to, for example, flexible printed circuit material, such as that used for circuit cables in computers. In this particular embodiment, the monitor device 60 is in a shape that conforms to the front bottom portion of the bra 20, at the lower portion of the bra cups (not numbered), allowing the band 61 of thin material of the monitor device 60 to comfortably slip underneath the front bottom portion of the bra 20.

The monitor device 60 includes a fastener mechanism, e.g., a tab 62a on the user's right side that is folded over to form a hook portion 63 that bends away from the user's body. The tab 62a is comprised of a relatively stiff material to maintain the hook shape of the folded tab. The folded tab 62a hooks over the bra 20 on the bra's right side strap 22a. Similarly, the device's left tab 62b hooks over the bra's left side strap 22b. The monitoring device 60 also has a center tab 62c configured to hook over a central portion 22c of the bra 20 (e.g., in the area of the bra between the two bra cups).

The monitoring device 60 includes sensors 30a and 30b on the side of the device facing the user (the "skin side"). ECG sensor 30a is on the skin side of tab 62a and ECG sensor 30b is on the skin side of tab 62b. The sensors 30a, 30b are connected by wires (not shown) to an electronics module 50 which includes an amplifier and wireless transmitter, as discussed above. The electronics module 50 is preferably located at the center tab 62c. The wires are integrated into monitoring device 60 to run through the body of the device 61, preferably using flexible circuit material. Alternative arrangements for sensors and electronics module 50 are possible. For instance, sensors could be located anywhere on the skin side of the band 61 of monitoring device 60.

The heart monitor device 60 uses the module 50 to transmit data 42 to a nearby computer, PDA 43 or wireless phone carried by the person wearing the device 20.

Figure 5:
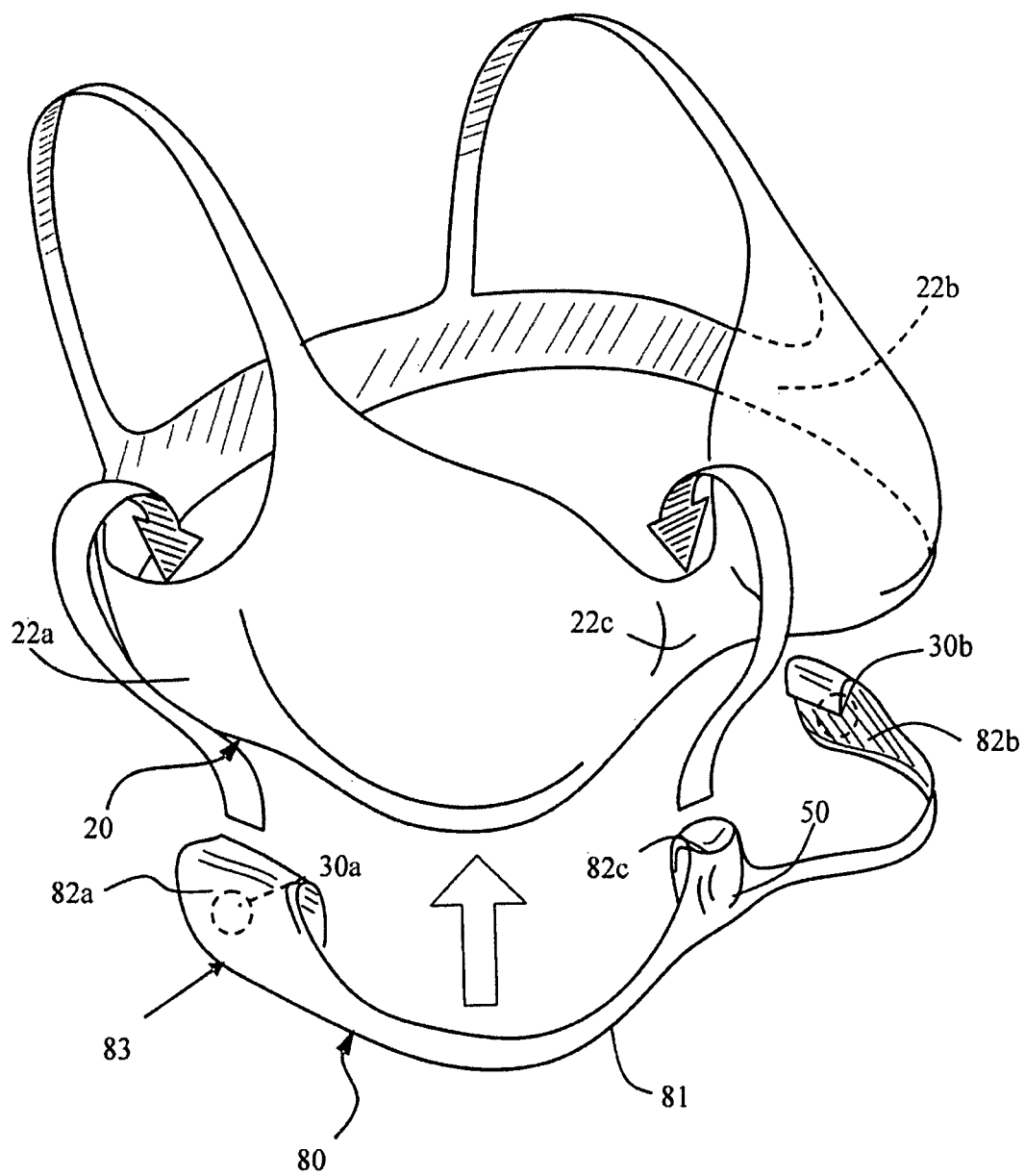
FIG. 5 is a perspective view of a bra with an alternative attachable monitor.

Referring now to FIG. 5, an alternative monitoring device 80, a variation of monitoring device 60 in FIG. 4 is shown. The monitoring device 80 is arranged to be worn outside of the bra 20. Again other types of clothing could be used instead of the bra. Depending on the underlying bra type, this embodiment may be more easily attachable to certain bras or may be more comfortable than monitoring device 60. When the user is already wearing the bra, it may be easier to attach monitoring device 80 than to attach monitoring device 60 which is slid underneath the bra cups.

The monitor device 80 is comprised of a thin, firm, flexible band 81 of material that may be similar to, for example, flexible printed circuit material, as mentioned above. In this particular embodiment, the monitor device 80 includes a fastener mechanism, e.g., a tab 82a on the user's right side that folds over inwards toward the user's body to form a hook portion 83 bending inwards (opposite to that of FIG. 4). As with the monitoring device 60, the tab 82a is comprised of a relatively stiff material to maintain the hook shape of the folded tab. The folded tab 82a hooks over the bra 20 on the bra's right side strap 22a and a similar arrangement of a left tab 82b hooks is provided for the bra's left side scrap 22b. The monitoring device 80 also has a center tab 82c configured to hook over a central portion 22c of the bra 20 (e.g., in the area of the bra between the two bra cups).

In addition, the monitoring device 80 includes sensors 30a and 30b on the side of the device facing the user (the "skin side"). ECG sensor 30a is on the skin side of tab 82a and BCG sensor 30b is on the skin side of tab 82b. The sensors 30a, 30b are connected by wires (not shown) to an electronics module, as discussed above.

Figure 6:
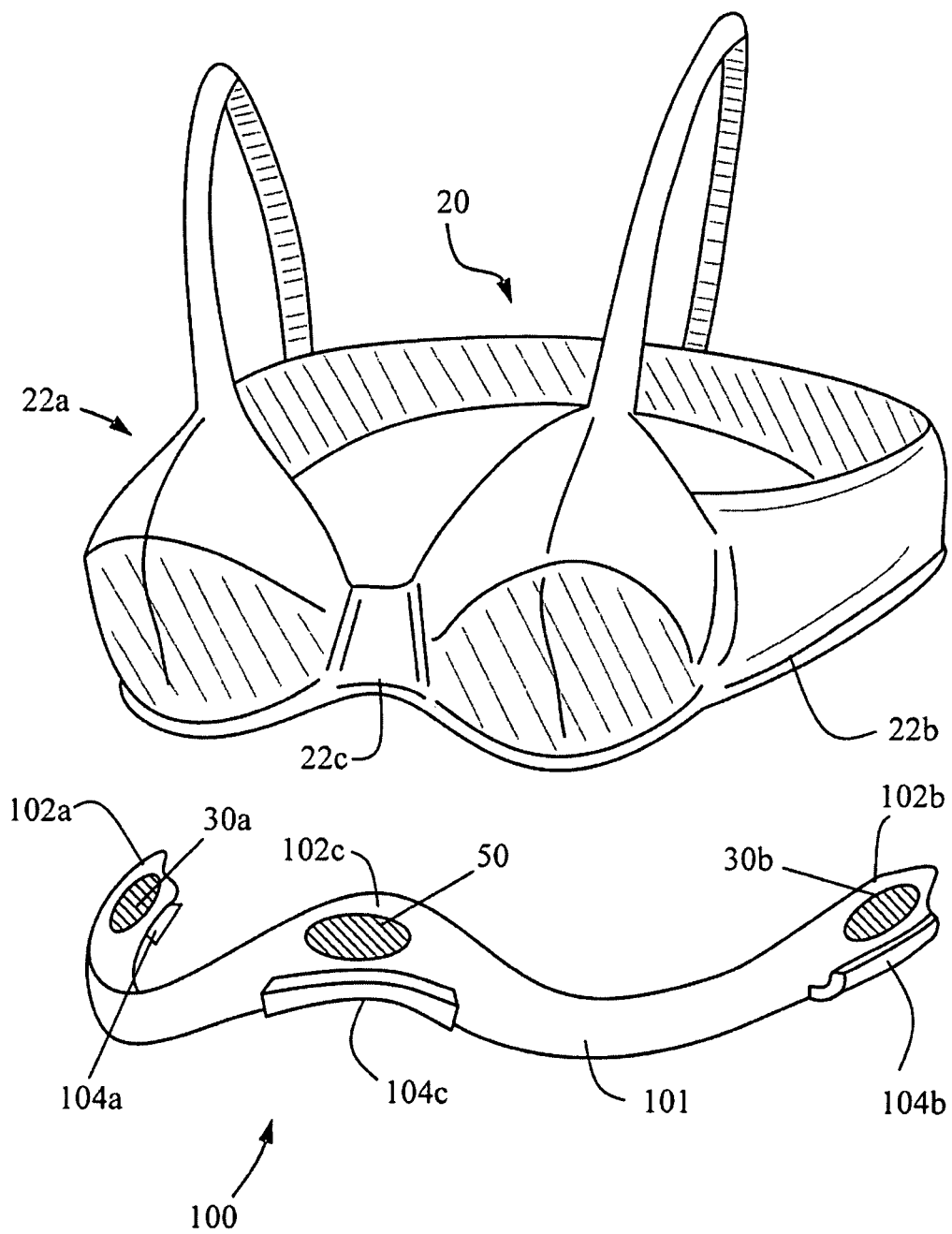
FIG. 6 is a perspective view of a bra with another attachable monitor.

Referring to FIG. 6, another variation 100 of a monitoring device that attaches to a bra is shown. In this variation, a clip mechanism is used to attach the monitoring device 100 to the bra 20, rather than use hooked tabs and gravity, as above. The monitoring device 100 is similar to those discussed in FIG. 4 in that the monitoring device 100 is shaped to conform to the front bottom portion of the bra 20, at the lower portion of the bra cups, and is comprised of a thin flexible, e.g., circuit board material, allowing monitoring device 100 to comfortably slip underneath the front bottom portion of the bra 20.

The device 100 has one end 102a that is held between the bra's right side strap 22a and the user's skin. At the right end 102a, a sensor 30a is integrated into the device. The other end of the device 202b is held under the bra's left side strap 22b and has a sensor 30b. The device 100 also has a central portion 102c that is secured under the bra's center 22c (the area of the bra between the two bra cups). The electronics module 50 is shown in this central portion 102c, although the sensors and electronics module could be at any location in the device 100.

The monitoring device has attachment mechanisms 104a-104c on the outside of the device 100 (e.g., clips or anchors) that attach to the bra.

Figure 7:
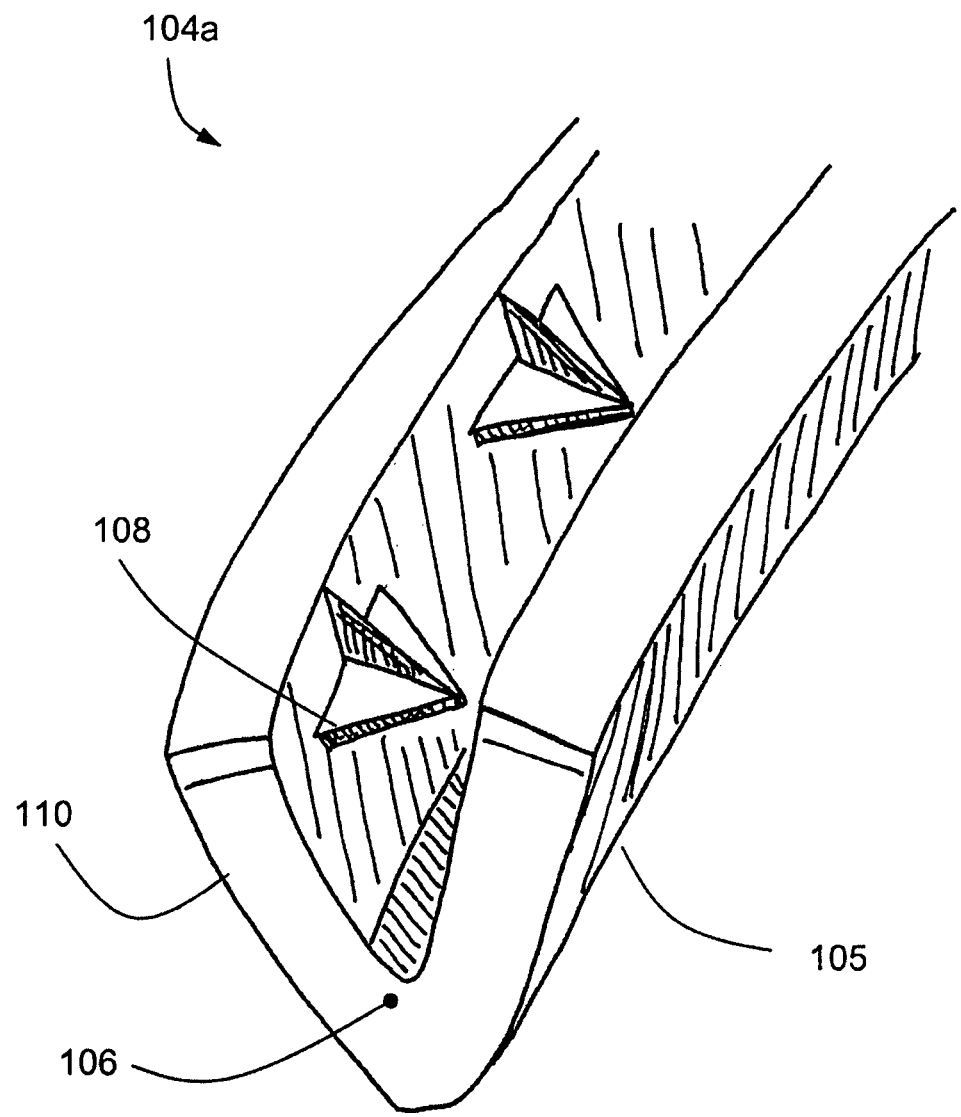
FIG. 7 is a perspective view of an attachment mechanism.

Referring now to FIG. 7, a detail of one embodiment of the attachment mechanism 104a-104c is shown. The mechanism 104a has a side 105 that attaches to the outside of the device 100. It is comprised of a plastic material that generally holds its shape but is flexible. The mechanism 104a is shaped to form a trough 106 that is large enough to accept the bottom seam of a bra. Inside the trough 106 are teeth 103 that are attached to the outer portion 110 of the mechanism. To attach the device 100 to the bra 20, the bra 20 is pulled into the trough 106. The trough 106 expands somewhat when the bra 20 is being inserted, because of the flexible nature of the mechanism 104a. A bra seam (not shown) of the bra 20 is pulled past the teeth 108 to hold the bra within the trough 106.

Figure 8:
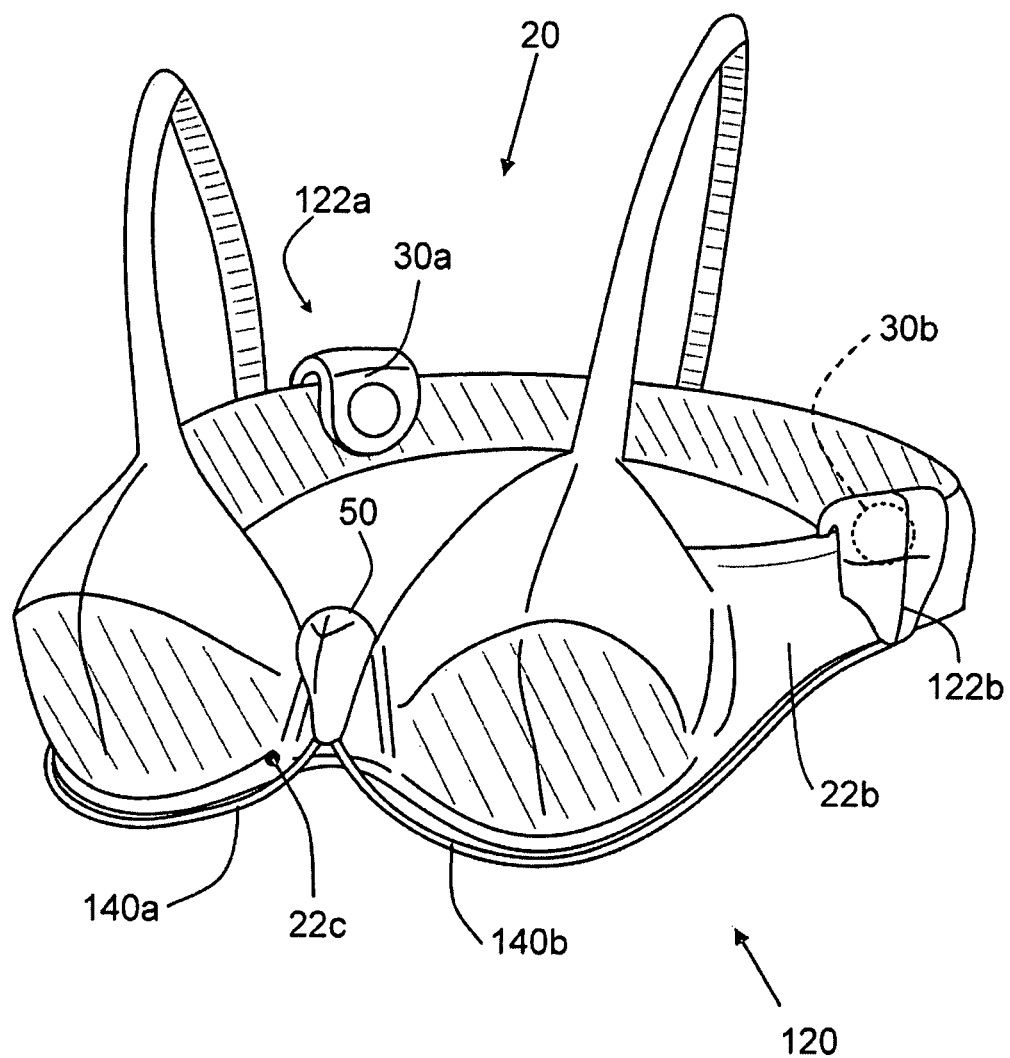
FIG. 8 is a perspective view of a bra with clip-on sensors.

Referring to FIG. 8, an alternative design 120 for the heart monitor is shown attached to a bra 20. The device 120 has an electronics module 50 that attaches to the central portion 22c of the bra 20 (between the two bra cups). The electronics module 50 is attached to two sensor assemblies 122a and 122b via wires 140a and 140b respectively. The wires can be shielded for electromagnetic interference. The shielding can extend to the sensor assembly. Sensor assembly 122a is shown worn on the user's back in a position for ischemia detection. On the skin side of the sensor assemblies is a wearable sensor: sensor assembly 122b having wearable sensor 30b.

The wires 140a and 140b could be permanently attached to the electronics module 50 and sensor assemblies or could have connectors such as a clip to attach to the sensor. For example, a removable connector on the sensor assemblies could accommodate different sensor assemblies for different activities. The electronics module could be attached to different locations than the one shown, for example, to the back of the bra or to the waistband of pants.

The sensor assemblies 122a and 122b could be attached to the bra straps 22a, 22b by a number of mechanisms, including a snap hinge that applies pressure to the bra strap and prevents the sensor from slipping off the bra strap; or the sensor assembly could be provided with teeth next to the bra strap to hold it in place. In addition, an elastic strap around the bra strap which attaches back to the assembly, Velcro straps, clips or other mechanisms could be used to hold the assembly in place on the bra strap.

A number of different sensor configurations are possible. For example, a sensor could be on the skin side of the electronics module 50. This sensor could take the place of the sensor on the user's right bra strap or could be used as an additional sensor. Sensors could be placed at different places on the bra 20.

The wires can be loosely coupled to the bra or wire guides can be provided in the bottom of the bra to hold the wires comfortably in place. The wire guides could be slots to hold the wires in place. Additionally, the bra could have clips to affix the wires to the bra. A bra could be provided with other accommodations for a removably attachable heart monitor device, as will be discussed below in FIG. 10.

The devices 60 (FIG. 4), 80 (FIG. 5), and 100 (FIG. 6) are shown as single unitary solid devices, with the sensors, electronics module and wiring being part of one solid assembly. Each aspect (sensors, electronics, wiring) could be a permanent part of the assembly 60, 80, 100. Similarly for device 120 (FIG. 8), the two sensors and the electronics module could each be unitary solid devices (as shown), permanently attached by the insulated wires to each other. Another option is to have some portion of the device 60, 80, 100, 120 removable and/or disposable, such as the electronics module, battery, or sensors. For example, having removable sensors would allow different types of sensors to be used for different activities. Exercise generates a lot of sweat, and desk work does not, so different sensor designs could be used depending on the anticipated level of perspiration.

Figure 9:
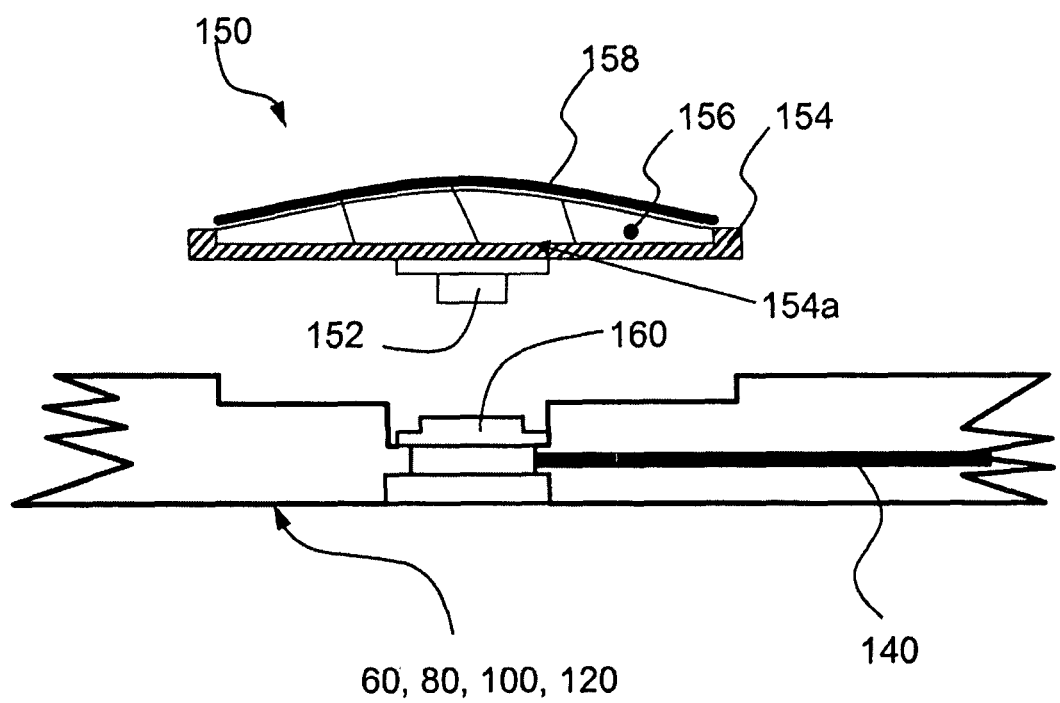
FIGS. 9-12 are cross-sectional views of removable sensors.

Referring to FIG. 9, a removable sensor 150 for sensing voltages from the skin to provide a signal for EGG monitoring is shown disposed in a portion of a monitor device 60 (FIG. 4), a monitor device 80 (FIG. 5), a monitor device 100 (FIG. 6) or a monitor device 120 (FIG. 8).

The removable sensor 150 has a snap 152. The snap 152 is attached to a sensor frame or housing 154 that is comprised of a firm but flexible material (e.g., rubber). The housing 154 is used to support a more flimsy, e.g. compliant low Young's modulus material that provides a sensor membrane 156. The sensing membrane 156 is comprised of an electrically conductive and flexible material, e.g., a conductive rubber or conductive silicone and is disposed inside the housing 154 and has a major surface thereof that is exposed so that the sensing membrane 156 can make contact with the skin. The sensing membrane 156 can be a flat or curved surface, as shown, to ensure secure and adequate contact with the skin.

The sensing membrane 156 may be temporarily covered with a conductive gel or a hydrogel film 158. A thin hydrogen film could be cut to size, and would provide excellent skin conduction to a wearable sensor material such as conductive silicone. Hydrogel, however, is not very durable and so the hydrogel might be used for, e.g., a day and then discarded and replaced.

The snap 152 is comprised of an electrically conductive material, e.g., a metal, conductive plastic, or hard conductive rubber and is disposed in intimate contact with the backside of the sensing membrane 156 to provide an electrical path for a signal from the sensing membrane 156 to a mating snap 160 on the device 60, 80, 100, or 120. This contact can be provided either by having the membrane 156 in intimate contact with a conductive back portion 154a of housing 154 or through an aperture (not shown) in the back portion 154a of the housing 154 that allows the snap 152 to be directly and electrically connected to the membrane 156.

The device 60, 80, 100, or 120 in this example would have an accommodation for the sensor 150. Here the accommodation is a mating snap 160. The removable sensor 150 thus attaches to the device by mating the snap 152 on the sensor 150 with the corresponding mating snap 160 on the device. In this configuration a wire 140 would be coupled to the mating snap 160 to carry the electrical signal to the electrical circuitry (FIG. 3). The snap 160 attaches to the device 60, 80, 100, or 120 by being disposed through an aperture in the material and crimped to surrounding material of the or device to hold the snap 160 in place.

The conductive snap arrangement just described could also be used to attach an aspect of a removable electronics module 50 to a device 60, 80, 100, or 120. Other attachment mechanisms can be used for those aspects that require electrical connectivity, for example, conductive Velcro or other hook and loop type fastener mechanisms could be used instead of a conductive snap.

Thus, sensors could be permanently attached to the heart monitor device, or could be removable. Parts or all of a removable sensor could be disposable (e.g. the hydrogel membrane).

A bra 10, 20 could be provided with accommodations for a removably attachable heart monitor device, including pockets, loops of material, slits and accommodations briefly mentioned above, which would help attach the heart monitor 60, 80, 100, 120 to the bra 10, 20, holding the heart monitor securely in place. Accommodations such as pockets, loops of material, slits and clips would allow the bra to be comfortably worn with or without the attachable heart monitor. The bra's accommodations could accommodate any aspect of the heart monitor 60, 80, 100, 120, that is, any portion could thread through the loop of material to be securely held in place, for example. The portion of the device that fits in the accommodation may be a section of the device assembly that includes the electronics module, wiring or sensors. As an example, referring back to FIG. 6, the bra 20 could be fashioned with pockets for the device 100, to hold the ends 102a and 102b, as an alternative to or an additional attachment mechanism to the clips 104a-104c. As another example, a bra accommodation such as a pocket in a bra 10, 20 may be especially useful to place and hold a sensor assembly in locations on the body that are known for quality ECG sensing. The face of the sensor can make contact with the skin of the user or alternatively capacitive-coupled sensors could be used.

Figure 10:
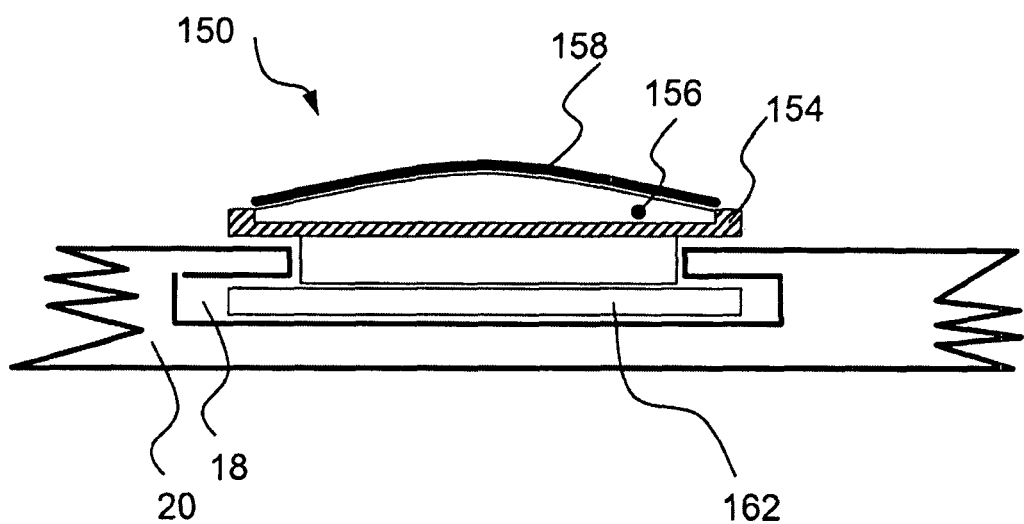

Referring to FIG. 10, an example of a bra 20 accommodation is shown. The bra 20 includes a pocket 18 (or a pouch or opening) to accommodate a sensor assembly 150 which is shaped to fit in the pocket. The pocket 18 is located in the side strap of the bra. Other locations in the bra or garment are possible. The pocket 18 is provided in the garment that is comprised of two layers of material. The sensor assembly 150 is shaped so that the bottom of the sensor assembly 162 fits in the pocket 18. The sensor assembly 150 may fit snuggly in the pocket 18, in which case the bra would provide the function of holding the sensor in place. Alternatively, the sensor assembly 150 could fit loosely in the pocket 18, with the bottom of the sensor assembly 150 preferably being coated with a low-friction material like Teflon, allowing the bra to move and stretch. The face of the sensor 150 would preferably be a high friction material to hold the sensor against the skin.

Figure 11:
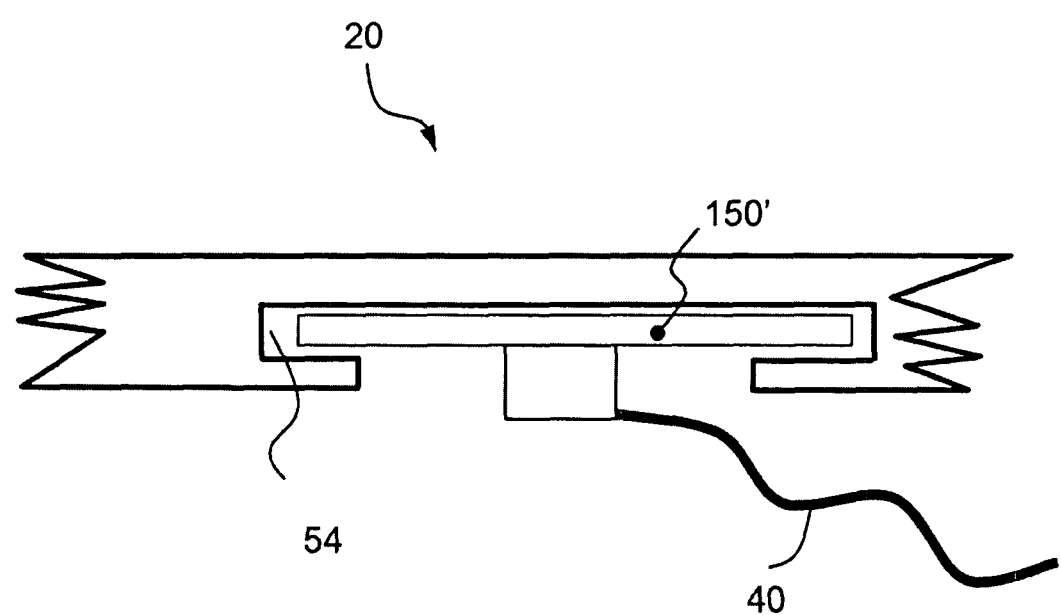

Referring to FIG. 11, an example of an arrangement with a sensor 150' that does not need direct skin contact, such as a capacitively coupled sensor for measuring ECG is shown. These types of sensors 150' could slip into a pocket 54 on the outside of the bra 20 and would not need to be in direct contact with the skin of the subject.

The heart monitor device is designed to place ECG sensors at physiologically interesting and useful places. The device can also hold other types of sensors, some of which can be of use in interpreting or processing the ECG signal. The device could incorporate motion sensors: detected motion can be used, for example, to invalidate portions of time in the ECG signal from a nearby ECG sensor when a large amount of motion is detected. ECG sensors can be used in conjunction with impedance plethysmography sensors to measure cardiac output. Sensors to measure surface skin temperature may add to the overall measure of user health.

The ECG sensors can be provided with a sensing material comprised of metal such as a conventional silver/silver chloride compound. While this metal material could be used, the metal material is somewhat inflexible, does not naturally stick to the skin, and can become slippery in the presence of perspiration. Other materials can be used such as conductive silicone, a wearable material commonly used for shock therapy electrodes, or conductive rubber provided by adding conductive, skin-friendly materials such as silver, gold or carbon to liquid rubber and molding the composition into the desired shape of a sensor. Other conductive materials such as conductive fabric provided by weaving fine threads of silver together with conventional fabric threads; or coating fabric threads with metal can be used.

Hydrogels can be used as a thin layer between any of these wearable sensor materials and the skin, as previously mentioned. These materials are suitable for sensing ECG signals from the skin without any skin preparation. The shape of the sensor can help maintain contact with the skin.

FIGS. 3 and 10 depict a smooth rounded sensor that would gently push against the skin to make contact with the skin of a subject.

Figure 12:
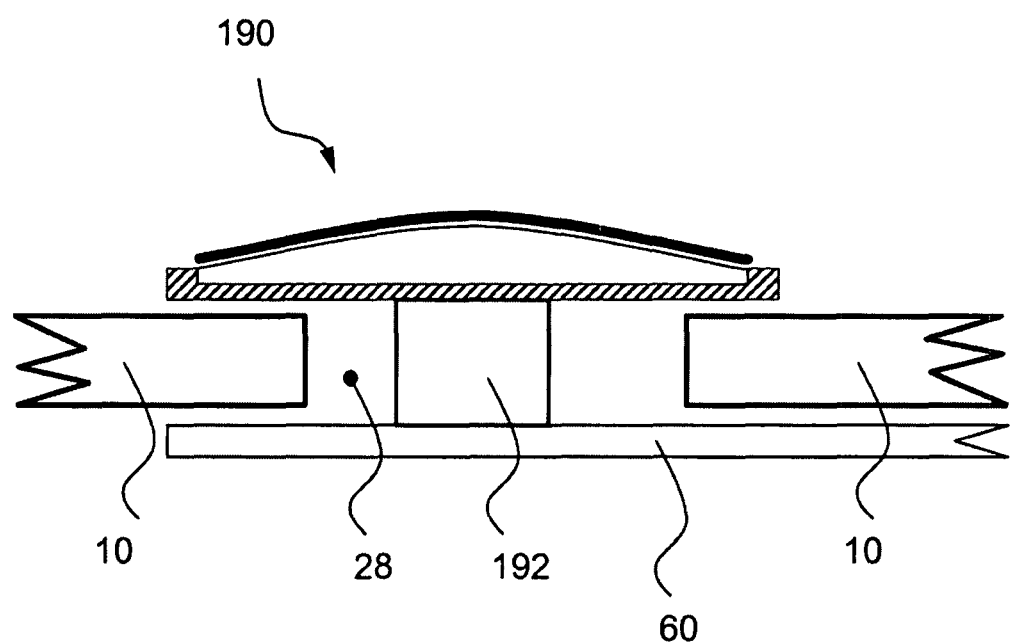

Referring to FIG. 12, a variation of the heart monitor device has sensors 190 configured with the structure of buttons, such that the button sensors can be slipped through slits 28 (like buttonholes) in some portion of the bra 10, for example, the chest band portion of a bra 10 such as that pictured in FIG. 1. The slit 28 allows a button sensor 190 to touch the skin, and also holds the sensor in place. For a suitable bra, adding these buttonholes is a very simple modification. The sensor 190 has a post 192 attached to the bottom of the sensor, which fits through the slit 28 in the bra 10 chest band. The post 192 is connected to the heart monitor device, e.g. 60 and the button hole in the chest band slips over the sensor and post.

Figure 13A:
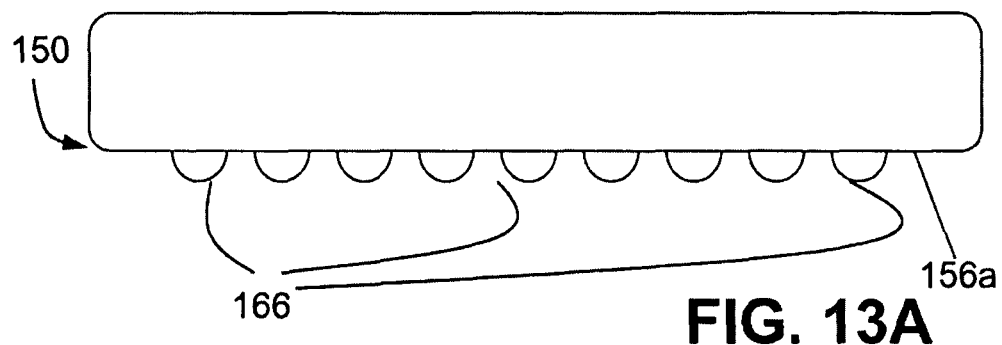
FIGS. 13A-13D are cross-sectional views showing possible surface preparation for sensor membranes.

FIGS. 13A-13D shows cross sections of sensor faces showing different textures. In FIG. 13A, the sensor 150 has a sensor face 156a with nubs or bumps 166 shaped like gumdrops on the surface of the sensor that touches the skin. This configuration of the surface would be suitable for working around body hair, as the nubs would have a good chance of pressing in between the hairs to reach the skin. Excessive sweat could also be channeled between the nubs 166.

Figure 13B:
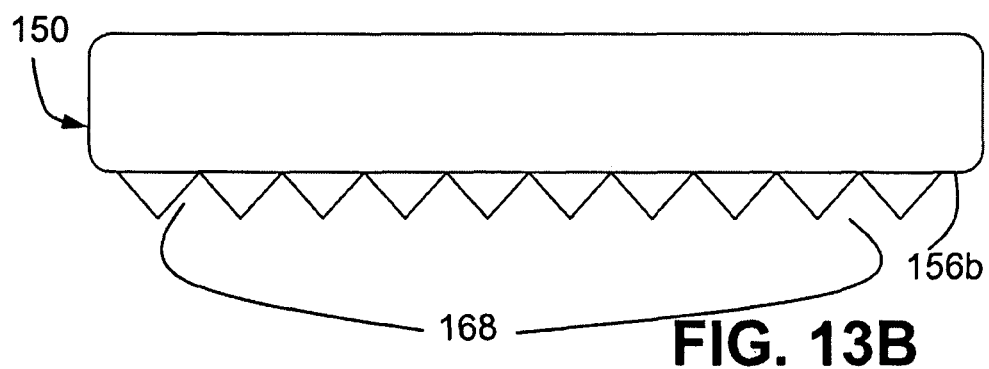

FIG. 13B shows a sensor face 156b having sharp ridges 168 which may be more suitable for reaching the skin through hair, than the nubs 166 of FIG. 13A. Sweat could also be channeled through the grooves in between the ridges 166.

Figure 13C:
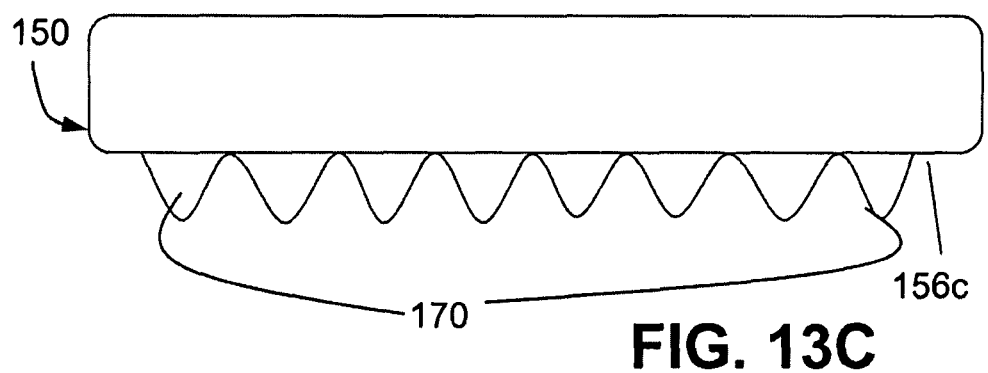
Figure 13D:
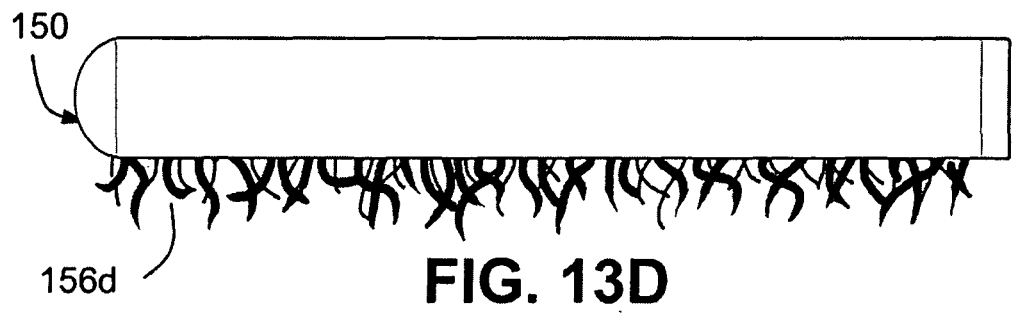

FIG. 13C shows another variation with grooves cut into the sensor face 156c forming softer ridges 170. In FIG. 13D conductive threads 156d are provided in the sensor face and help maintain contact with the skin even when the sensor is sliding across the surface of the skin.

Figure 14A:
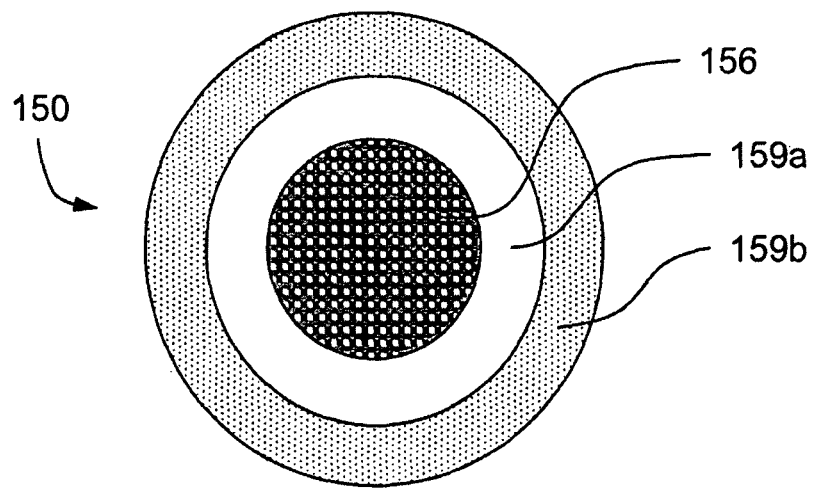
FIGS. 14A and 14B are plan and cross-sectional views of an alternative sensor.
Figure 14B:
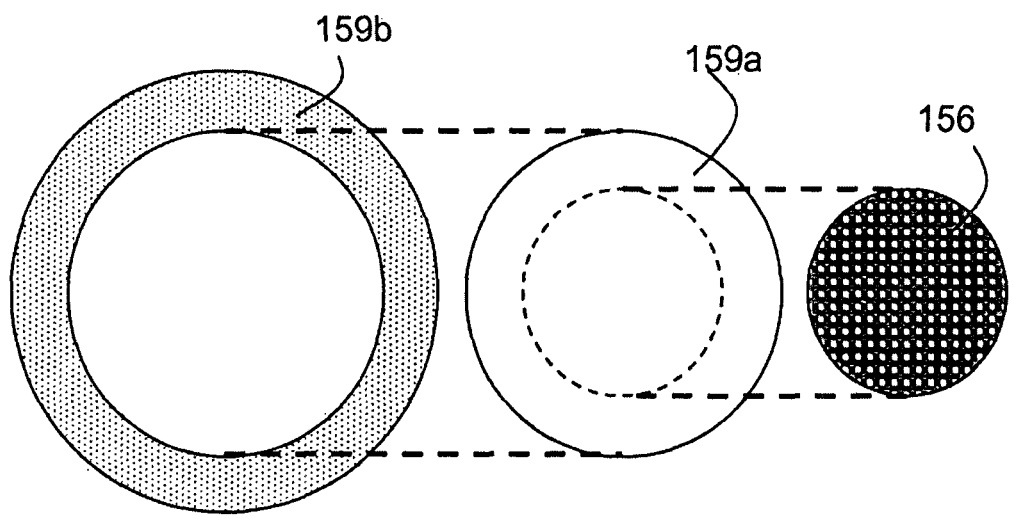

Referring to FIG. 14, to prevent the sensor 150 from sliding, a ring of sticky or high-friction material 159a such as rubber or soft silicone could foe placed around the sensing material 156. The friction ring 159a may be made of waterproof material (silicone, for example), which may also induce sweat.

Sweat is a good conductor for ECG sensors, and inducing a little sweat can help maintain skin contact and conductivity. However, if there is too much sweat, the sensor may slide against the skin, inducing noise in the signal, and the excess sweat may be uncomfortable. For this reason it may be beneficial to have a sweat absorbing ring 159b that surrounds the rest of the sensor. The sweat-absorbing material 155b can be made of cotton, for example.

The sensing material may be in the shape of a flat disk, as shown in FIG. 14A, and made of a conductive fabric which can absorb some sweat. These conductive fabrics tend to dry out when the user is not perspiring, which may drastically reduce the sensor's conductivity. One solution is to apply a waterproof or water resistant backing 159a to the sensing material 156, to help keep the sensing material 156 damp by sweat. The material 159a extends beyond the edges of the sensing material 156 to make contact with the skin and provide the high-friction function, while also providing a water resistant barrier around the sensing material 156 to induce sweat. For applications where large amounts of sweat are anticipated, the sweat disk 159a could be constructed of water resistant material that allows some evaporation. The sweat-absorbing ring 159b is shown in FIG. 15B does not overlap any other part of the sensor, but is a separate ring to ensure direct shin contact and prevent sweat from dripping down from the sensor.

The sensing material 156, friction ring 159a and sweat-absorbing ring 159b are shown as circular shapes. However, these elements could be rectangular or any other shape or provided in alternating strips, and still provide the same functions.

The ideal physiological sensor would be able to induce enough sweat for good conduction, but wick away excess sweat. In the absence of the ideal, users may desire to have different sensors for different activities, different amounts of sweat, and differences in comfort. Users may differ in how dry their skin is, how much body hair they have, or how much they sweat, requiring different sensors. To work in the presence of sweat or hair, an uneven surface will allow parts of the sensor to reach the skin and make good contact.

The devices 60, 80, 100, or 120 carry comfortable sensors that need not use adhesive against the skin and can stay in place against the skin. The mechanisms that hold the sensors against the skin include a tensile force that is imparted to the sensors by the bra 20. Also, in some embodiments, the sensors will tend to stay in place against the body by providing the sensor faces with a relatively high-friction surface to minimize slippage against the skin. The bra 20 allows sensors to be placed at physiologically useful places on the body. In some embodiments, the sensors may also have slightly sticky or tacky surface to help to hold the sensors in place against the skin.

Referring now to FIG. 15, there are several possible ECG lead configurations with the attachable heart monitor 60, 80, 100, or 120. Using ECG sensors at the position of V6 and V6R, a lead from V6 to V6R will provide ECG with good amplitude. V6 to V2 would also be good, and adding a ground sensor at V6R would help signal stability. Additional leads could use sensors at V3, V4 and V5, which are very close to the heart and provide good amplitude. A sensor on the back chest band of the bra may provide information about ST changes in the ECG over time, which can be an indication of myocardial ischemia.

A number of embodiments of the invention have been described. Nevertheless, it will be understood that various modifications may be made without departing from the spirit and scope of the invention.

What is claimed is:

1. A garment accessory comprises:
   a member having first and second ends and a length between the first and second ends, with the length of the member between the first and second ends being approximately half of the circumference of the chest of a subject that the member is configured to be positioned on;
   a pair of fastener mechanisms disposed in proximity to the first and second ends of the member, the fastener mechanisms configured to attach the member to an article of clothing at portions of the article of clothing that are at the sides of the subject, when the article of clothing is worn by the subject; and
   at least a pair of sensors supported at the pair of fastener mechanisms of the member, the sensors having sensor membranes of the sensors configured to rest against the skin of the subject;
   the fastener mechanisms comprising tabs comprised of a stiff material of a sufficient stiffness and having fold portions to attach to the article of clothing, with the fold portions disposed to fold away from the skin of the subject.

2. The garment accessory of claim 1, wherein the member further has a fastener mechanism disposed at the center of the member.

3. The garment accessory of claim 2 wherein the fastener mechanisms at the first and second ends of the member and the center of the member are configured to couple the member to a brassiere.

4. The garment accessory of claim 3 wherein the member is comprised of a thin, firm, flexible band of material, the garment accessory further comprising:
   a set of conductors carried in the flexible band of material; and
   a circuit arrangement electrically coupled to the pair of sensors by the set of conductors, the circuit arrangement carried by the member.

5. The garment accessory of claim 4 wherein the circuit arrangement includes a wireless transmitter.

6. The garment accessory of claim 1 wherein the pair of sensors are removable from the member.

7. The garment accessory of claim 1 wherein the fastener mechanisms further comprise at least one of hooks, clips, elastic band, hook and loop fasteners or snaps.

8. The garment accessory of claim 1 wherein the tabs of the fastener mechanisms maintain a hook shape when bent to form hook mechanisms that hook over portions of the article of clothing.

9. The garment accessory of claim 1 wherein the tabs of the fastener mechanisms fold to form clips disposed on the bottom outside edge of the garment accessory, configured such that when the garment accessory is underneath the article of clothing that encircles the torso of the subject, the clips attach to the bottom edge of the article of clothing.

10. The garment accessory of claim 1 wherein the sensors are at least one of ECG sensors, motion sensors, body temperature sensors or impedance plethysmography sensors.

11. The garment accessory of claim 1 wherein the article of clothing that the garment accessory is configured to attach to is a brassiere.

12. The garment accessory of claim 1 wherein the garment accessory is configured to be secured on side straps of a brassiere.

13. The garment accessory of claim 1 wherein the sensor membranes are in electrical contact with a mating snap, the sensor membranes comprised of an electrically conductive, flexible material.

14. The garment accessory of claim 13 wherein each sensor membrane is comprised of at least one of conductive rubber or conductive silicone.

15. The garment accessory of claim 13 wherein each sensor membrane has a major surface thereof that is exposed to make contact with the skin of the subject, the major surface being curved.

16. The garment accessory of claim 13 wherein each sensor membrane has a major surface thereof that is exposed to make contact with the skin of the subject, the major surface being flat.

17. The garment accessory of claim 13 wherein each sensor membrane has a major surface covered with a conductive gel film.

18. The garment accessory of claim 13 further comprising:
   at least a pair of snaps, each snap comprising of an electrically conductive material disposed in intimate contact with a first surface of the sensor membrane to provide an electrical path for a signal from the sensor membrane, each snap engaging a mating snap supported by the member.

19. The garment accessory of claim 13 wherein each sensor further comprises a sensor frame comprised of a firm, flexible material supporting the sensor membrane.

20. The garment accessory of claim 13 wherein each sensor membrane comprises:
   a water resistant material to induce sweat.

21. The garment accessory of claim 13 further comprising:
   a layer of sweat-absorbing material disposed adjacent to each sensor membrane.

22. A heart monitor device comprises:
   a member having first and second ends and a length between the first and second ends, with the length of the member between the first and second ends being approximately half of the circumference of the chest of a subject that the member is configured to be positioned on;
   a pair of fastener mechanisms disposed on fastener mechanism portions disposed at ends of the member, the fastener mechanisms to attach the heart monitor device to side portions of a brassiere at portions of the brassiere that are at the sides of the subject when the heart monitor is worn by the subject;
   a pair of physiological sensors, carried by the member, the pair of physiological sensors disposed in proximity to the fastener mechanism portions of the member; and
   an electronics module electrically coupled to the pair of physiological sensors through conductors disposed in the member;
   the fastener mechanisms comprising tabs comprised of a stiff material of a sufficient stiffness and having fold portions to attach to the article of clothing, with the fold portions disposed to fold away from the skin of the subject.

23. The device of claim 22 wherein the electronics module is supported at a central portion of the length of the member.

24. The device of claim 23 wherein the electronics module includes a signal amplifier.

25. The device of claim 23 wherein the electronics module includes a wireless transmitter.

26. The device of claim 22 wherein the fastener mechanisms further comprise at least one of hooks, clips, elastic band, hook and loop fasteners or snaps.

27. The device of claim 22 wherein the sensors are at least one of ECG sensors, motion sensors, body temperature sensors or impedance plethysmography sensors.

28. The device of claim 22, further comprising a central fastener mechanism configured to hold at least part of the member in place underneath a lower portion of a front of the brassiere, in a region between cup portions of the brassiere.

29. The device of claim 28 wherein the pair of fastener mechanisms and the central fastener mechanism of the device are configured as at least one of loops or pouch portions to attach to corresponding portions of the brassiere.

30. The device of claim 23 wherein the tabs of the fastener mechanisms to maintain a hook shape when bent to form hook mechanisms that hook over portions of the brassiere.

* * * * *